United States Patent [19]
Larrabee et al.

[11] Patent Number: 4,645,111
[45] Date of Patent: Feb. 24, 1987

[54] SURGICAL STAPLER WITH RETRACTABLE ANVIL

[75] Inventors: Edward W. Larrabee, Bronxville, N.Y.; Charles M. Huck, Pottersville, N.J.

[73] Assignee: Howmedica, Inc., New York, N.Y.

[21] Appl. No.: 281,320

[22] Filed: Jul. 8, 1981

[51] Int. Cl.[4] .............................................. B25C 5/04
[52] U.S. Cl. ....................................... 227/19; 227/83; 227/88; 227/120; 227/DIG. 1
[58] Field of Search ..................... 227/19, 83, 88, 120, 227/131, 134, 145, DIG. 1; 128/334 R

[56] References Cited

U.S. PATENT DOCUMENTS

| | | | |
|---|---|---|---|
| 2,420,830 | 5/1947 | Maynard | 227/134 |
| 2,432,853 | 12/1947 | Barclay | 227/145 X |
| 2,707,783 | 5/1955 | Sullivan | 227/19 X |
| 4,109,844 | 8/1978 | Becht | 227/120 |
| 4,179,057 | 12/1979 | Becht et al. | 227/19 |
| 4,349,143 | 9/1982 | Ewig | 227/134 X |
| 4,364,507 | 12/1982 | Savino | 227/DIG. 1 X |

*Primary Examiner*—Fred Silverberg
*Attorney, Agent, or Firm*—Connolly and Hutz

[57] ABSTRACT

A surgical stapler includes a supply of staples which are fed one at a time to the discharge opening where a driver in the stapler housing bends the staple around the anvil, the anvil being retracted within the housing away from the discharge opening as the driver completes the bending operation.

12 Claims, 15 Drawing Figures

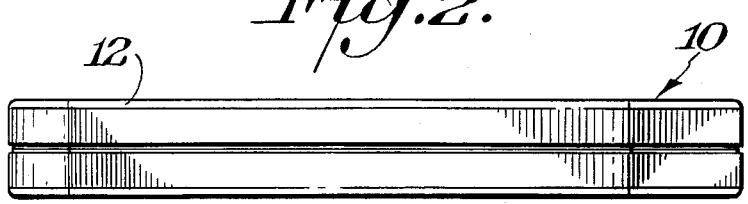
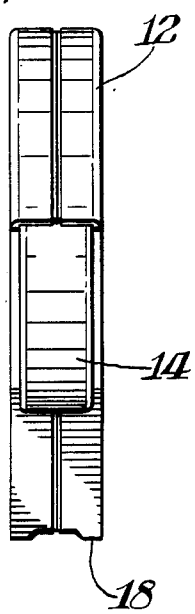
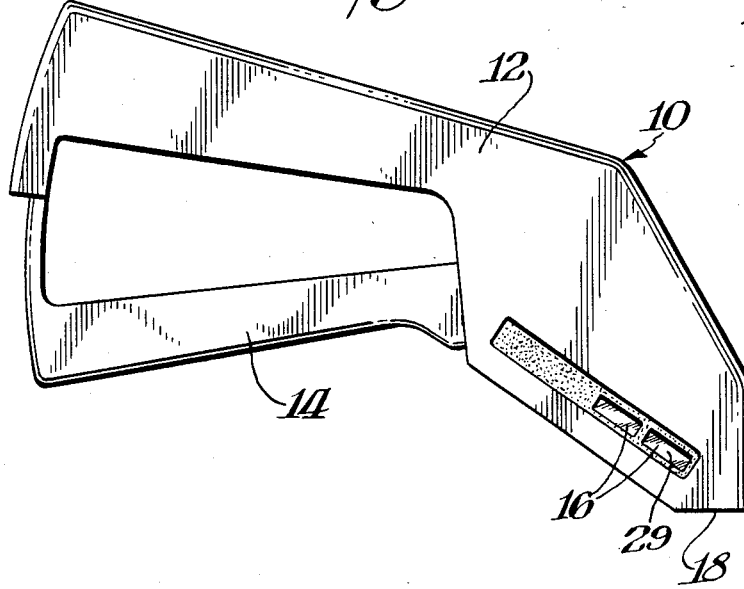
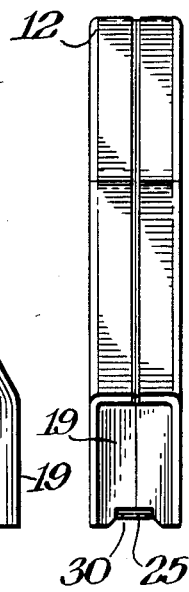
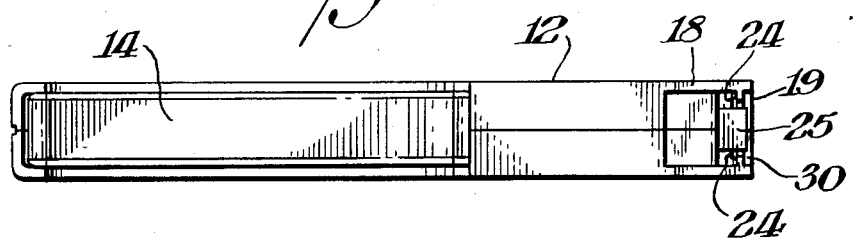

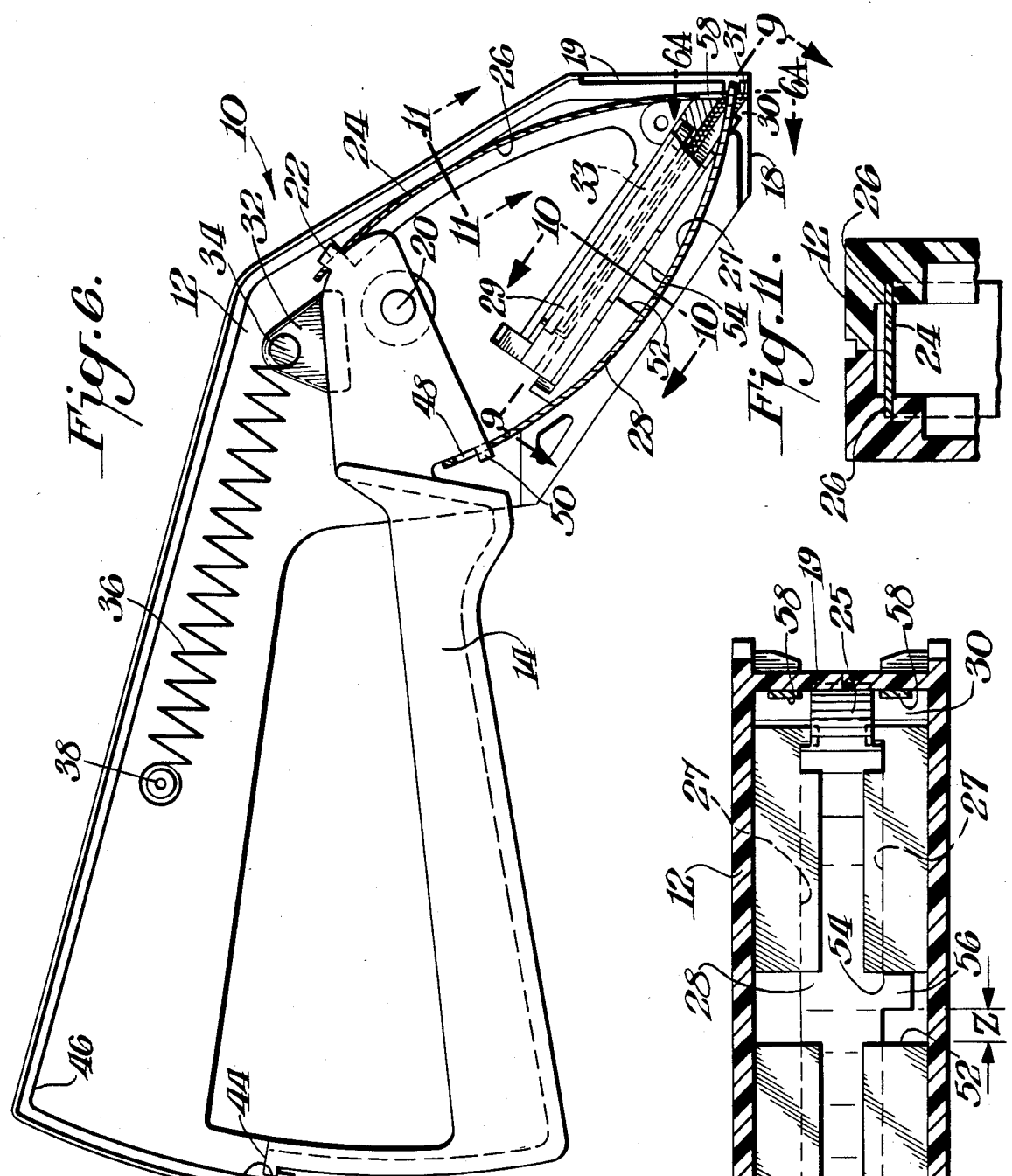

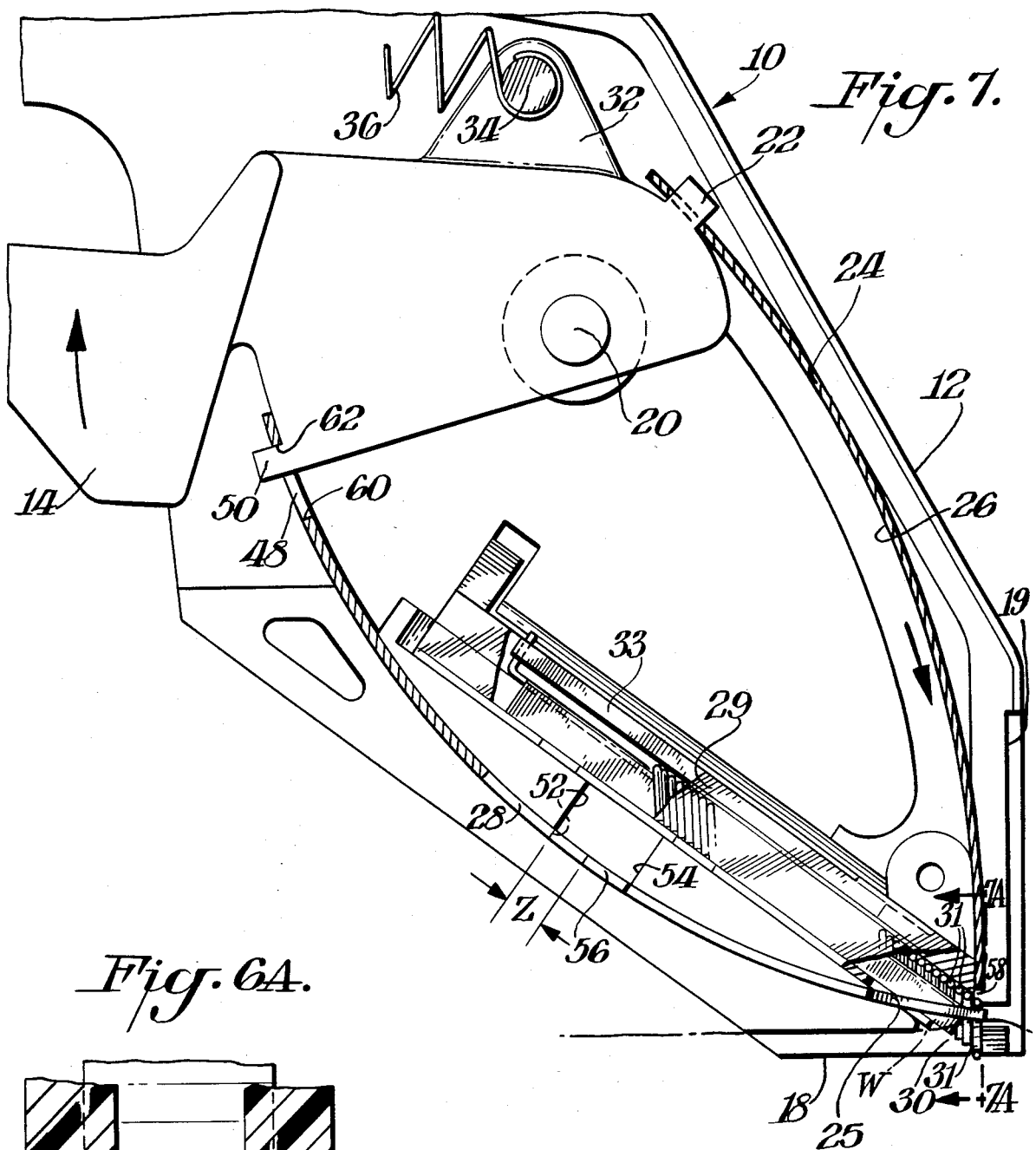
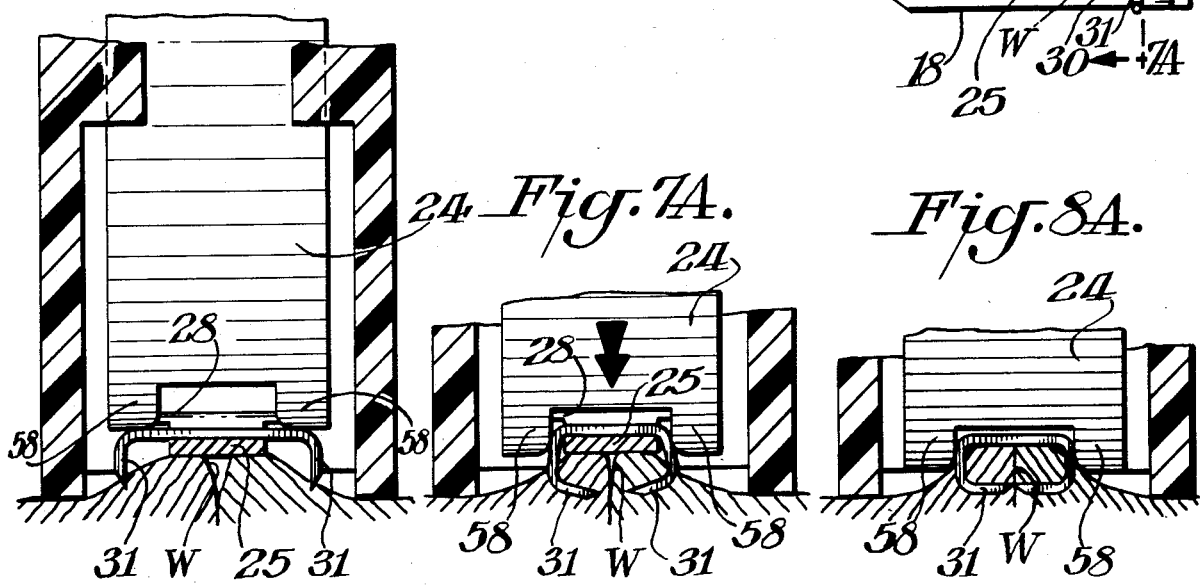

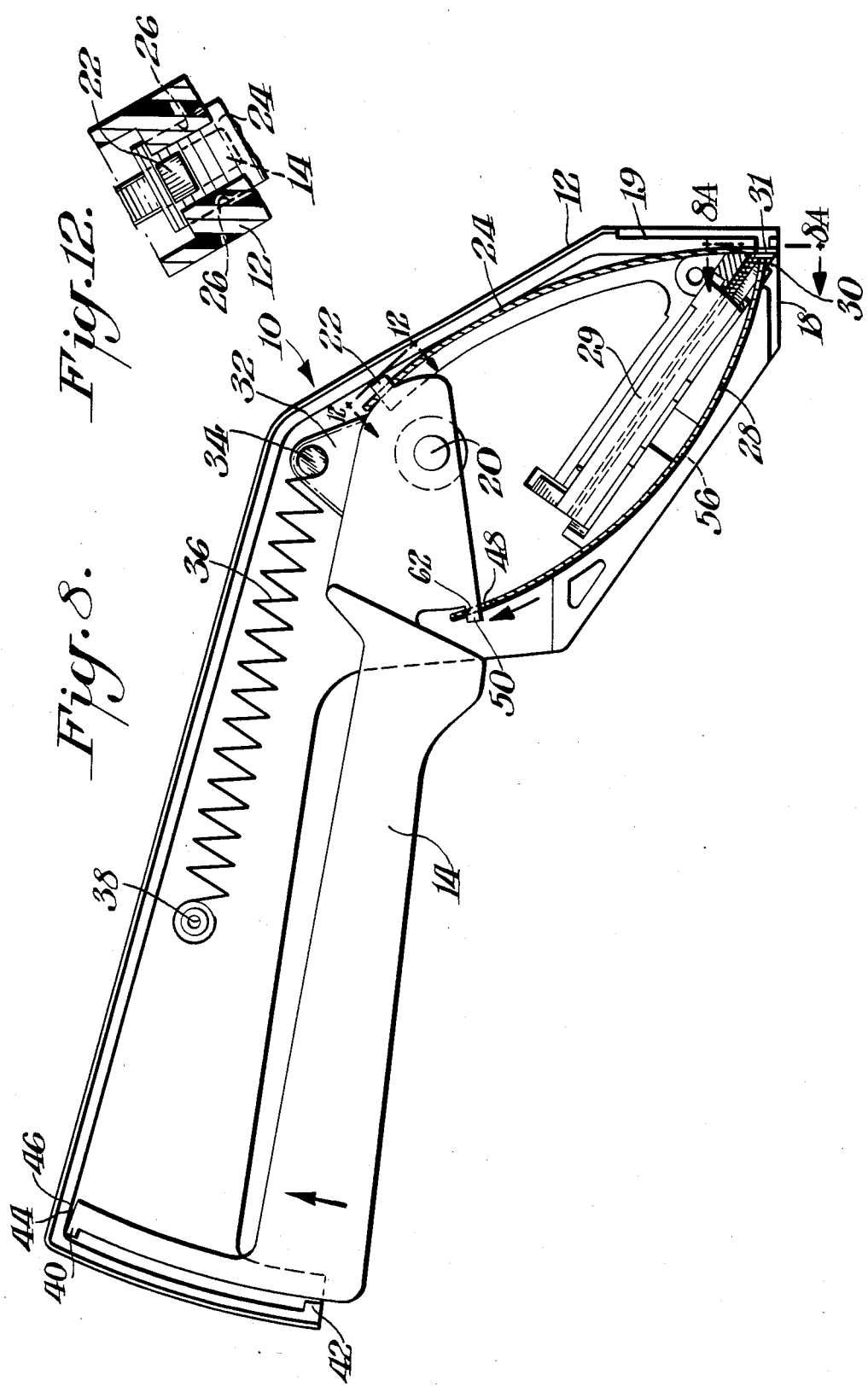

SURGICAL STAPLER WITH RETRACTABLE ANVIL

BACKGROUND OF THE INVENTION

There presently exist various forms of hand held staplers which are used for various purposes. One such use is for closing a wound or incision in the skin or facia of a patient. Such surgical staplers generally utilize a supply of staples such as in magazine or cartridge form whereby the staples are fed to the forward end of the stapler, a handle frequently being utilized to actuate a driver which bends the staple about an anvil and into the patient. A disadvantage with such arrangement is that when the bending operation is complete, it is necessary to move the stapler so as to withdraw the fixed anvil from beneath the crown of the staple; failure to perform this maneuver may result in tearing the formed staple out of the tissue of the wound site. The stapler is then moved to the desired location for applying the next staple. U.S. Pat. No. 4,179,057 is typical of such stapler.

SUMMARY OF THE INVENTION

An object of this invention is to provide a stapler which may be conveniently used without the drawbacks of the prior art.

A further object of this invention is to provide such a stapler which is particularly adapted for use as a surgical skin stapler.

A still further object of this invention is to provide such a stapler which can be conveniently moved to the next work site.

In accordance with this invention, the stapler includes a supply of staples, a driver and an anvil in the stapler housing. A significant feature of the invention, however, is that the anvil is made retractable so that at the time of completion of the staple bending operation, the anvil is retracted within the housing, which permits the stapler to be moved in any direction for the next stapling sequence.

In a preferred form of this invention, the driver and anvil are secured to a rotatable handle in such a manner that upon rotation of the handle the driver is urged forward and the anvil remains stationary for a period of time until the staple bending operation is complete, continued rotation of the handle causing retraction of the anvil.

BRIEF DESCRIPTON OF THE DRAWINGS

The above and other objects, features and advantages of the present invention will be apparent from the following detailed description of an embodiment thereof in conjunction with the accompanying drawings wherein like reference numerals indicate like structures throughout the several views.

FIG. 1 is a side elevation view of a stapler in accordance with the invention;

FIG. 2 is a top plan view of the stapler shown in FIG. 1;

FIGS. 3-4 are front and rear elevation views, respectively, of the stapler shown in FIGS. 1-2;

FIG. 5 is a bottom plan view of the stapler shown in FIGS. 1-4;

FIG. 6 is a side elevation view partly in section with a portion of the housing removed from the stapler shown in FIGS. 1-5;

FIG. 6A is a cross-sectional view taken through FIG. 6 along the line 6A—6A showing one phase of operation of the stapler shown in FIGS. 1-6;

FIG. 7 is a view similar to FIG. 6 showing a subsequent phase of operation;

FIG. 7A is a cross-sectional view taken through FIG. 7 along the line 7A—7A;

FIG. 8 is a view similar to FIGS. 6 and 7 showing a further phase of operation;

FIG. 8A is a cross-sectional view taken through FIG. 8 along the line 8A—8A;

FIGS. 9-11 are cross-sectional views taken through FIG. 6 along the lines 9—9, 10—10 and 11—11, respectively, with the cassette removed from FIG. 9; and FIG. 12 is a cross-sectional view taken through FIG. 8 along the line 12—12.

DESCRIPTION OF THE PREFERRED EMBODIMENTS

FIGS. 1-5 illustrate a stapler 10 in accordance with this invention which may be used for various purposes but which is particularly designed to function as a surgical stapler. As indicated therein, stapler 10 includes a housing 12 which may be made in any suitable manner. In a preferred form of this invention, the housing 12 is comprised of left and right plastic body moldings. Stapler 10 also includes a rotatable handle 14 which may be injection molded. As later described, a window 16 is formed in housing 12 so that the supply of staples therein is readily visible. Housing 12 includes a flat end portion 18 having a discharge opening so that end portion 18 may be located on the work site for applying the staples one at a time.

FIG. 6 shows the various components of stapler 10 in the initial phase of operation, that is, in the phase of operation before any bending of the staples takes place. As indicated therein, handle 14 is pivotally mounted about pin 20 secured within housing 12. Handle 14 includes a pin or other suitable projection 22 which is integrally molded thereto near the center of rotation and fits into a complementary hole in driver 24, as further shown in FIG. 12. Driver 24 is preferably a curved steel plate which, as shown in FIG. 11, rides in guide slots 26, 26 in housing 12. As later described, handle 14 has mounted thereto anvil 28 in such a manner that a delayed action retraction results by the squeezing of handle 14 upwardly into housing 12. Anvil 28 is a crescent shaped steel plate such as shown in FIG. 9.

Mounted within housing 12 is a supply of staples preferably mounted in a clear plastic cartridge or cassette 29, such as commercially available under the name Proximate (TM), which feeds the staples one at a time toward discharge opening 30 at end portion 18 under the influence of spring 33.

Handle 14 has a lug or ear 32 formed thereon with a pin 34 to which is mounted reset spring 36 which is secured to pin 38 in housing 12 for urging handle 14 to its downward or nonoperative position shown in FIG. 6. Handle 14 is maintained in this position by means of flange 40 abutting against inturned flange 42 of housing 12. Handle 14 may be squeezed upwardly into housing 12 until edge 44 of handle 14 contacts edge 46 of housing 12; conversely, handle 14 is prevented from being withdrawn from housing 12 by abutting flanges 40, 42.

As shown in FIGS. 6 and 9, anvil 28 includes an elongated slot 48. Handle 14, in turn, includes an integrally molded pin or projection 50 which is located within anvil slot 48. As best shown in FIG. 9, housing 12 also includes a slot or opening defined by walls 52, 54, and anvil 28 includes a projection 56 which is disposed between walls 52 and 54.

FIGS. 6, 6A and 9 show the condition of stapler 10 during the initial phase of operation. As indicated in FIGS. 6 and 6A, staple 31 from cassette 29 is located above anvil tongue 25 with driver 24 in turn positioned above staple 31. The prongs of staple 31 are positioned on opposite sides of the incision or wound W (FIG. 6A) with forming or crimping fingers 58, 58 at the end of driver 24 located at the corners of staple 31. At this stage of operation, projection 56 of anvil 28 is located against wall 54, and pin 50 is located against end 60 of anvil slot 48 (FIG. 9).

To begin the stapling operation, handle 14 is squeezed upwardly. FIGS. 7 and 7A show the change in position of the various components during this phase of operation. As indicated in FIG. 7A, driver 24 is moved downwardly, and forming fingers 58, 58 bend the prongs of staple 31 inwardly toward each other as staple 31 is formed around anvil tongue 25 so that the prongs enter the skin or facia of the patient. The upward rotation of handle 14 causes pin 50 to move in anvil slot 48 away from end 60. During this stage of operation, anvil 28 remains stationary with projection 56 juxtaposed wall 54. This lost motion or delayed action whereby pin 50 is moved without causing any movement of anvil 28 is indicated by the distance K of FIG. 9.

Continued upward squeezing of handle 14 results in the components being in the condition shown in FIGS. 8 and 8A wherein anvil 28 is retracted away from opening 30. This retractable motion is achieved by pin 50 contacting end 62 of anvil slot 48, whereupon pin 50 and anvil 28 move jointly to the position shown in phantom in FIG. 9. The total movement of pin 50 within anvil slot 48, represented by distance C, is sufficient to permit anvil 28 to be retracted clear of staple 31 immediately upon completion of the bending operation so that, as shown in FIG. 8A, the bending operation of staple 31 is completed with the anvil being totally retracted from the operative site. During its motion, anvil 28 is guided in slots 27, 27.

During the retractive movement of anvil 28, projection 56 is moved away from wall 54 toward wall 52. This movement is indicated in FIGS. 7 and 9 by the distance Z. As is clear from FIG. 9, distance Z is equal to distance C minus distance K. Distance Z is preferably selected so that projection 56 contacts wall 52 as handle edge 44 contacts housing edge 46 (FIG. 8) whereby the abutting surfaces (projection 56 contacting wall 52 and handle edge 44 contacting housing edge 46) provide a double means of limiting the distance that anvil 28 is retracted within housing 12.

As the handle motion is reversed under the influence of reset spring 36, driver 24 is retracted causing the row of staples 31 to advance and, during the final portion of return motion, anvil 28 is returned to its active position beneath driver 24 as pin 50 contacts wall 60 of anvil slot 48.

As previously indicated, the present invention makes use of known components, such as a readily available staple supply means located in housing 12 in such a manner that the vertical end wall 19 of housing 12 acts as an abutment for the foremost staple 31 being ejected from cassette 29.

Stapler 10 provides a number of convenient advantages. For example, stapler 10 can be formed of sufficiently low cost material so as to be disposable. To complement this disposability feature, stapler 10 includes the aforenoted windows 16 whereby the number of staples 31 in transparent cassette 29 is readily visible so that the operator can determine at any time approximately how many more stapling operations can be accomplished with stapler 10. The cooperation and location of handle 14 with respect to housing 12 is also particularly advantageous in that the user's hand would be located a substantial distance from the incision or wound W to minimize obstruction of the work site by the manipulation of stapler 10. Advantageously, handle 14 also forms a common drive means for both the driver 24 and the anvil 28 to effectively retract anvil 28 immediately upon the completion of the staple bending or forming operation so that the staple 31 is completely freed from the device and the user is correspondingly free to readily move stapler 10 in any direction for the next stapling operation.

We claim:

1. A stapler comprising a housing, said housing having a discharge opening for placement at a work site, means in said housing for disposing staples one at a time at said discharge opening, an anvil in said housing for being disposed at said discharge opening beneath a staple thereat, a driver movably mounted in said housing for bending said staple aroung said anvil at said discharge opening, and means for retracting said anvil within said housing away from said discharge opening as said driver completes the bending of said staple, said anvil retracting means being coupled to said driver by common drive means in such a manner that actuation of said driver automatically causes retraction of said anvil.

2. The stapler of claim 1 including a handle rotatably mounted to said housing with said driver and said anvil being operatively secured to said handle, whereby rotation of said handle causes movement of said driver and said anvil to function as said common drive means.

3. The stapler of claim 2 wherein said driver is fixedly mounted to said handle for joint movement therewith and said anvil is mounted to said handle by lost motion drive means.

4. The stapler of claim 1 wherein said means for disposing staples includes a transparent cassette having a supply of staples therein and said housing has at least one window disposed in the area of said cassette, whereby the amount of staples in said cassette is visibly apparent from outside said housing.

5. The stapler of claim 1 including guide grooves of or guiding said anvil and said driver in their respective movements.

6. The stapler of claim 1 wherein said common drive means causes said anvil to slide away from the operative site during retraction of said anvil.

7. A stapler comprising a housing said housing having a discharge opening for placement at a work site, means in said housing for disposing staples one at a time at said discharge opening, an anvil in said housing for being disposed at said discharge opening beneath a staple thereat, a driver movably mounted in said housing for bending said staple around said anvil at said discharge opening, means for retracting said anvil within said housing away from said discharge opening as said driver completes the bending of said staple, common drive means for moving both said driver and said anvil, and handle rotatably mounted to said housing with said driver and said anvil being operatively secured to said handle whereby rotation of said handle causes movement of said driver and said anvil to function as said common drive means, said driver being fixedly mounted to said handle for joint movement therewith and said anvil being mounted to said handle by lost motion drive means, a pin being secured to said handle for joint movement therewith, said anvil having a slot, and said handle pin being disposed in said anvil slot.

8. The stapler of claim 7 including stop means for limiting the amount of movement of said anvil.

9. The stapler of claim 8 including a slot in said housing and a projection on said anvil disposed in said housing slot, whereby said housing slot and said anvil projection comprise said stop means.

10. The stapler of claim 7 wherein said driver and said anvil are each a plate mounted for movement in an arcuate path.

11. The stapler of claim 7 wherein said handle is mounted for telescopic movement into and out of said housing with complementary stop means on said housing and said handle to prevent said handle from moving completely out of said housing, said driver and said anvil being mounted to said handle at spaced portions thereof near the center of rotation of said handle.

12. The stapler of claim 11 wherein spring means urges said handle in a downward direction for movement out of said housing, and said complementary stop means comprises an inturned flange on said housing and an outwardly extending flange on said handle.

* * * * *